United States Patent [19]

Takahashi

[11] 4,294,233
[45] Oct. 13, 1981

[54] SLACK ABSORBING DEVICE FOR AN ENDOSCOPE

[75] Inventor: Nagashige Takahashi, Tokyo, Japan

[73] Assignee: Kabushiki Kaisha Medos Kenkyusho, Tokyo, Japan

[21] Appl. No.: 27,418

[22] Filed: Apr. 5, 1979

[30] Foreign Application Priority Data

Apr. 12, 1978 [JP] Japan ............................ 53/47865[U]

[51] Int. Cl.³ .............................................. A61B 1/00
[52] U.S. Cl. ......................................... 128/4; 403/43
[58] Field of Search ....................................... 128/3-8; 403/43, 46, 48

[56] References Cited

U.S. PATENT DOCUMENTS

| 421,570 | 2/1890 | Heiser | 403/43 X |
| 2,353,250 | 7/1944 | Le Doyen | 403/43 |
| 3,832,072 | 8/1974 | Mazur | 403/46 |
| 3,892,228 | 7/1975 | Mitsui | 128/4 |
| 4,203,430 | 5/1980 | Takahashi | 128/4 |

FOREIGN PATENT DOCUMENTS 2752325 7/1978 Fed. Rep. of Germany .......... 128/4

OTHER PUBLICATIONS

Webster's New Collegiate Dictionary, p. 918, (1956).

Primary Examiner—Robert W. Michell
Assistant Examiner—Arthur S. Rose
Attorney, Agent, or Firm—Sughrue, Mion, Zinn, Macpeak and Seas

[57] ABSTRACT

A slack absorbing device in the bending operation mechanism of an endoscope. Slack absorbing members are moved along the passage ways of connecting wires as the bending section is bent. Each slack absorbing member has a long groove extending along the direction of movement of said slack absorbing member and a theaded groove formed in a portion of the long groove. Threaded rods connect the ends of the wires extending to the bending section provided in the top end part of the endoscope in such a manner that the threaded rods are moved together with the wires at least when the wires are pulled towards the manual operating section. A part of each threaded groove is cut off so that the threaded rod can engage the threaded groove by aligning the theaded rod, in a direction corresponding to the direction of movement of the wire, and placing it into the groove.

7 Claims, 4 Drawing Figures

SLACK ABSORBING DEVICE FOR AN ENDOSCOPE

BACKGROUND OF THE INVENTION

This invention relates to a device for absorbing the slack of operating wires employed in a device for bending the top end part of an endoscope.

In order to select a suitable passage for the top end part of an endoscope when it is inserted into the body cavity, or to direct the observing window of the endoscope as desired when the body cavity is observed, it is necessary to appropriately change, or bend, the direction of the top end part of the endoscope. For this purpose, a remote operation device is provided in which a pair of wires are extended from the top end part of the endoscope to the manual operating section thereof. The direction of the observing winding can be changed by selectively tightening or loosening the wires at the manual operating section.

However, in the bending operation by the remote operation device, there may be play between the operation of the manual operating section and the bending operation of the top end part of the endoscope. This is highly undesirable, because the operation of an endoscope of this type requires a delicate operation of the top end part. Accordingly, it is necessary that the coupling between the operating sections have no play, and that especially, the wires have no play when they are moved to be tightened.

In view of the flexibility of the passage way through which the wire is inserted, a twisted wire is generally employed. Therefore, the wire is liable to become elongated not only by the repetitive use under tension but also by the untwisting of the wire itself. Accordingly, even if the wires are set tightened in advance, they will slacken with the lapse of time. Thus, it is necessary to provide a slack absorbing device for absorbing the elongation of the wire.

Within the prior art, devices for adjusting the flexing of the bending section of an endoscope are generally known. One such device is described in U.S. Pat. No. 3,892,228. In that prior art patent, a wire sag prevention device shown in FIG. 7 and in the overall system in FIG. 3 comprises a housing 28 containing sliding members 29 coupled to wire elements 17a, 17b and a wire wrapped around pulley 21. A plug member 30 is screwed into the housing and by adjustment thereof, the effective internal length of the cavity in the housing is varied. This restricts the degree of movement of sliding elements 29 to adjust for elongation in the wires. Also, a plugging member 31 can be inserted between plug 30 and one sliding element to further reduce the amount of movement by decreasing, ever further the internal length when the wires have excessively stretched. One of the disadvantages of this device is that "play" exists by having two sliding elements 29 within housing 28. Hence, if the wires 17a, 17b are stretched they may not abut the plug 30 but rather may move within the housing until a sufficient rotation of pulley 21 moves the housing a sufficient distance to engage the slider. Hence, displacement of the housing 28 may not in all cases effectuate corresponding movement of wires 17a, 17b.

Also, with this device, elongation due to untwisting of the wires cannot be prevented because the sliders are not constrained against rotation in the housing. When such untwisting occurs, although further tightening can be accomplished, retwisting of the wires cannot be attained. The use of plug members 31 also adds unnecessary complicating elements easily misplaced or incorrectly positioned.

Since re-adjustment is required for absorbing the elongation of the wire which is caused with the lapse of time, a requirement exists that the slack absorbing device be capable of easy re-adjustment.

With the device for changing the bending section of the top end part of the endoscope with a pair of wires as described above, the wire which is loosened by the operation of this device is slackened, and more specifically the part of the wire which is extended in the operating section of the device is slackened. It is also necessary to absorb the slack of the wire during the operation of the endoscope as described above.

SUMMARY OF THE INVENTION

Accordingly, an object of this invention is to provide a device for absorbing the slack of the wire as described above, and more particularly to provide a device for absorbing the play of the wire caused with the lapse of time, in which the adjustment for absorbing the play can be readily and positively achieved.

It is another object of this invention to provide for a wire slack adjusting device that is easily operated and has a wide range of adjustment.

These and other object of this invention are accomplished by means of a slack absorbing mechanism having slack absorbing members moved along the passage ways of connecting wires as the bending section is bent. Each slack absorbing member has a long groove extending along the direction of movement of said slack absorbing member and a threaded groove formed in a portion of the long groove. Threaded rods connect the ends of the wires extended to the bending section provided in the top end part of the endoscope in such a manner that the threaded rods are moved together with the wires at least when the wires are pulled towards the manual operating section. A part of each threaded groove is cut off so that the threaded rod can be engaged with the threaded groove by aligning the threaded rod, in a direction with the direction of movement of the wire and a placing it into the threaded groove.

This invention will be described in greater detail with reference to its preferred embodiment shown in the accompanying drawing.

DESCRIPTION OF THE PREFERRED EMBODIMENTS

Figure 1:
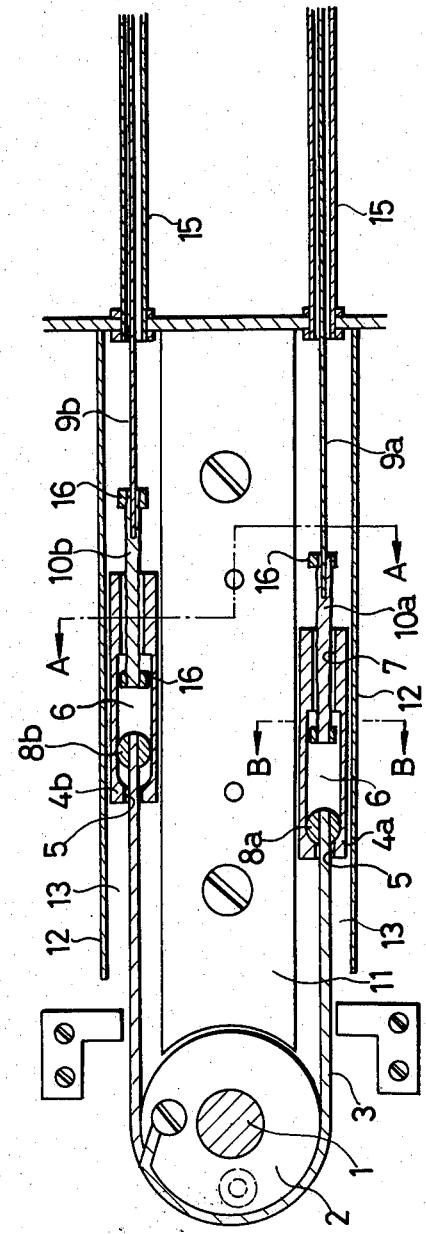
FIG. 1 is a sectional side view showing the essential components of a manual operating section body in one example of a slack absorbing device according to this invention.

FIG. 1 is a fragmental sectional view showing the essential components of a manual operating section in one example of a slack absorbing device according to the invention. As shown in FIG. 1, a pulley 2 is fixedly secured to an operating dial shaft 1 arranged in the manual operating section. An operating wire 3 is wound on the pulley 2 in such a manner that it does not slip on the pulley 2. Both ends of the operating wire 3 are extended to bend absorbing members 4a and 4b, respectively.

Figure 2:
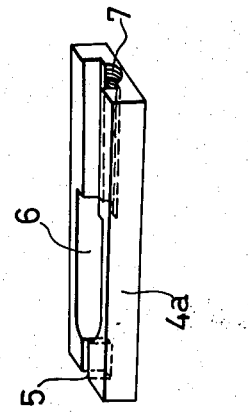
FIG. 2 is an enlarged perspective view showing one example of a slack absorbing member employed in the device according to the invention.
Figure 3:
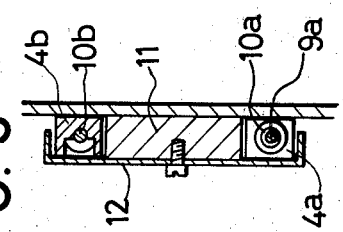
FIG. 3 is a sectional side view taken along line A—A in FIG. 1.
Figure 4:
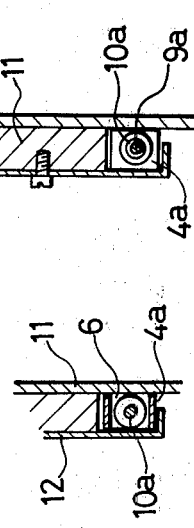
FIG. 4 is also a sectional side view taken along line B—B in FIG. 1.

FIG. 2 is an enlarged perspective view showing the slack absorbing member 4a or 4b. Each of the slack absorbing members is made of a relatively thick metal plate. In the metal plate, a relatively short wire groove 5 is cut at one end, a relatively long groove 6 wider than the groove 5 is cut in succession with the groove 5 is formed, and a threaded groove 7 is cut at the other end portion in succession following the groove 6. Thus, grooves 5, 6 and 7 are provided along the longitudinal axis of the metal plate. As shown in FIG. 2, the threaded groove 7 comprises an upper half which is a simple groove, and the lower half which is threaded.

Referring back to FIG. 1, locking pieces 8a and 8b are fixedly fastened to the two end portions of the operating wire 3. The locking pieces 8a and 8b are slidably inserted in the long grooves 6 of the slack absorbing members 4a and 4b, by placing the wire 3 in the wire grooves 5, respectively.

In FIG. 1, reference characters 9a and 9b designate a pair of wires connected to the bending operation section provided at the top end part of an endoscope (not shown). The other ends of the wires 9a and 9b are fixedly secured to threaded rods 10a and 10b, respectively. The threaded rods 10a and 10b engage the threaded parts of the threaded grooves 7 of the slack absorbing members 4a and 4b, respectively.

The slack absorbing member 4a connected between one end of the wire 3 and the rod 10a, and the slack absorbing member 4b connected between the other end of the wire 3 and the rod 10b are freely slidable by the wire operation in passage ways 13 surrounded by a stationary member 11, a cover member 12 and their respective side edges. The passageways 13 form parts of the movement path for the wire 3 and slack absorbing members 4a and 4b in the manual operating section.

In FIG. 1, reference numeral 15 designates pipes accommodating the wires 9a and 9b. Reference numeral 16 designates end pieces screwed over the two end portions of each of the threaded rods 10a and 10b.

In the device thus constructed according to the invention, the mechanism on the side of the manual operating section body and the mechanism on the side of the top end part of the endoscope are assembled separately. The two ends of the wire 3 on the side of the manual operating section body are connected through the slack absorbing members 4a and 4b in the passage ways 13 to the wires 9a and 9b on the side of the top end part, respectively.

In this connecting operation, first the locking pieces 8a and 8b at the both ends of the wire 3 are slidably fitted in the long grooves 6 of the slack absorbing members 4a and 4b, respectively, as shown in FIG. 1. Then, the threaded rods 10a and 10b connected respectively to the wires 9a and 9b are placed in the threaded grooves 7 by passing them through the upper halves of the threaded grooves. They are then engaged with the threaded parts of the grooves 7, respectively. This operation should be carried out by pulling the threaded rods 10a and 10b towards the manual operating section so that the wires 9a and 9b connected to the top end part have sufficient tension.

When the wires 9a and 9b have been suficiently tensioned the positions of the threaded rods 10a and 10b in the threaded grooves 7 of the slack absorbing members 4a and 4b may sometimes be different from each other. However, if the threaded part of the threaded rod coincides in position with the thread part of the threaded groove, then they can be positively engaged with each other even if the positions of the threaded rods 10a and 10b in the threaded grooves 7 are different from each other as described above.

Thus, the pair of wires 9a and 9b are suitably secured to the respective slack absorbing members 4a and 4b without slack. Thereafter, the cover member 12, etc. are installed.

In the case when the bending operation is effected by turning the operating dial shaft 1, the line constituted by one end of the wire 3 and one of the wires 9a and 9b, for instance the wire 9a, is tightened. As a result, the locking piece 8a of the wire 3 is locked at one end of the long groove 7 as shown in FIG. 1, and the slack absorbing member 4a is pulled to the left in FIG. 1 while the wire 9a is pulled in the same direction through the threaded rod 10a engaged with the threaded groove 7. As the wire 9a is pulled in this manner, the top end part of the endoscope is bent towards the side where the end of the wire 9a is connected that is, downward.

On the other hand, the line which is constituted by the other end of the wire 3 and the wire 9b is slackened. Accordingly, a difference results between the amount of movement of the wire 9b which is moved toward the top end part as the top end part is bent and the amount of movement of the end of the wire 3 which is fed as the pulley 2 is turned. This difference is absorbed by the sliding operation of the locking piece 8b in the long groove 6 of the slack absorbing member 4, and therefore the wires 3 and 9b are never slackened during the bending operation.

The bending operation in the opposite direction can be achieved by turning the operating dial shaft 1 and accordingly the pulley 2 in the opposite direction, similarly as in the above-described case.

As the top end part of the endoscope is repeatedly bent, the wires, especially the long wires 9a and 9b, are repeatedly tightened and loosened resulting in permanent elongation. As a result, play may be caused in turning the knob. In this case, it is necessary to re-adjust the mounting positions of the wires 9a and 9b with respect to the slack absorbing members 4a and 4b. This re-adjustment can be achieved by the following method: First, the cover member 12 is removed, and then the threaded rods 10a and 10b are removed, from the slack absorbing members 4a and 4b by picking them up. After the wires 9a and 9b have been sufficiently tightened, the threaded rods 10a and 10b are placed on and engaged with the slack absorbing members 4a and 4b, respectively. Thus, the permanent elongation of the wires 9a and 9b can be absorbed.

As indicated, when the wire is used for a long time, it becomes elongated. However, untwisting of the wire may be one of the causes elongating the wire. This difficulty can be overcome by threading the threaded rods 10a and 10b connected to the wires in a direction opposite to the twisting direction of the wires (being Z-twisted, in general). In this case, the threaded rods 10a and 10b engaged with the threaded sections of the threaded grooves 7 are moved to tighten the wires as the threaded rods 10a and 10b are turned by the rotations of the wires. This is a result of untwisting which is significantly caused when the wires are initially tightened. Thus, the slack due to the elongation can be effectively absorbed and retwisting effectuated.

As is apparent from the above description, in the device according to this invention, the slack absorbing members are provided in the middle parts of the wires connecting the manual operating section and the top end part of the endoscope, so that the slack absorbing members connect these wires. Accordingly, it is possible that the mechanism on the side of the manual operating section and the machining on the side of the top end part can be assembled separately, and the wires on the both sides can be connected through the slack absorbing members. Thus, the assembling and design of these mechanisms are relatively simple owing to the feature of this wire connecting method. In addition, machining and mounting of the slack absorbing members, the parts at the ends of the wires, and relevant parts can be achieved separately. Accordingly, the workability is improved, and assembly can be readily achieved.

As described before, the threaded groove in the slack absorbing member has the threaded part in the lower half. Therefore, the threaded rod can be positively engaged with the threaded groove merely by placing the threaded rod on the threaded part of the threaded groove; that is, the threaded rod is held by the threaded groove with a high degree of friction. It should be noted that especially, the position of the threaded rod can be changed freely within the range that the threaded rod can engaged with the threaded groove. In addition, this positioning can be achieved substantially steplessly. Therefore, the length of the wire can be quickly and effectively adjusted. Accordingly, in combination with the feature that the assembling work is very simple, the elongation of the wire which is caused by the use for a long period of time can be readily adjusted.

In the device according to this, it is unnecessary to twist the wire when connected to the slack absorbing member. Therefore, a difficulty such as wire twisting trouble is never caused. Furthermore, it is unnecessary to use any special tools such as an assembling tool to connect the wire to the slack absorbing member. Thus, a secondary effect of the invention is that the mechanisms can be readily disassembled for repair.

In the device described above, the threaded rod is welded to the wire by brazing; however, the wire may be connected to the threaded rod according to the following method: The wire is passed through a through-hole cut in the threaded rod, and an end piece is fixedly secured to the end of the wire so that the wire may not be removed from the threaded rod.

It is apparent that other changes and modifications can be made without departing from the essential scope of this invention.

What is claimed is:

1. An endoscope having a distal and a proximal end, a manual operating section adjacent the proximal end and a bending section adjacent the distal end, a plurality of elongated passageways in said manual operating section extending lengthwise of said endoscope, a plurality of slack absorbing members, one said member being mounted for slidable movement in each said passageway, said slack absorbing members being connected to said operating section such that they are movable along the length of said endoscope within said passageways as said operating section is operated, each of said slack absorbing members being elongated in the direction of said movement and having a centrally located elongated groove extending in the direction of said movement, said groove having a threaded portion, at least two twisted wires each having two ends, one end of each wire being connected to said bending section and the other ends of said wires being connected to different ones of said slack absorbing members such that when said manual operating section is operated said wires are moved in such a way that said bending section bends, said wires having threaded rods connected to said other ends whereby said threaded rods are moved together with said wires at least when said wires are pulled towards said manual operating section, said passageways being partially defined by a removable cover member, said threaded rods being provided with an end piece, each threaded groove having an open portion extending for at least the length of said threaded portion such that when said cover member is removed each of said threaded rods are engageable with a respective threaded groove by positioning said threaded rods above said threaded grooves and lowering said rods into said grooves, said cover member and said end pieces being positioned and sized such that they prevent removal of said rods from said grooves.

2. An endoscope as claimed in claim 1, in which said threaded rod is threaded in a direction opposite to the direction of twist of said wire.

3. An endoscope as in claim 1 wherein the open portion of each threaded groove forms an enlarged groove having a transverse width greater than said end piece.

4. An endoscope as in claim 1 wherein said slack absorbing members have a central groove which is wider than said threaded groove.

5. An endoscope as in claim 4 further comprising a pulley member disposed in said manual operating section, an operating wire wrapped around said pulley, each end of said wire being positioned in a respective elongated groove of a slack absorbing member.

6. An endoscope as in claim 5 further comprising locking members fastened to each end of said operating wire, said locking members slidably disposed in said central groove.

7. The device of claims 2, 3, or 1 wherein said threaded rods are adjustably connected to said slack absorbing members by means of interengaging screw threads.

* * * * *